US005283038A

United States Patent [19]
Seymour

[11] Patent Number: 5,283,038
[45] Date of Patent: Feb. 1, 1994

[54] FLUID SAMPLING AND TESTING DEVICE

[75] Inventor: Eugene H. Seymour, Pacific Palisades, Calif.

[73] Assignee: Saliva Diagnostic Systems, Inc., Vancouver, Wash.

[21] Appl. No.: 775,195

[22] Filed: Oct. 11, 1991

Related U.S. Application Data

[63] Continuation-in-part of Ser. No. 629,278, Dec. 18, 1990, abandoned, which is a continuation-in-part of Ser. No. 722,333, Jun. 25, 1991, abandoned.

[51] Int. Cl.$^5$ .................. G01N 33/48; C12M 1/28; C12M 1/30
[52] U.S. Cl. .................. 422/101; 422/58; 422/99; 422/102; 128/760; 435/294; 435/295
[58] Field of Search .............. 128/632, 760, 762, 769; 422/58, 99–102; 435/294, 295

[56] References Cited

U.S. PATENT DOCUMENTS

| | | | |
|---|---|---|---|
| 3,086,527 | 4/1963 | Forrest | 128/263 |
| 3,117,569 | 1/1964 | Wegner | 604/1 X |
| 3,163,160 | 12/1964 | Cohen | 604/1 X |
| 3,449,081 | 6/1969 | Hughes | 422/101 X |
| 3,773,035 | 11/1973 | Aronoff | 604/1 X |
| 3,776,220 | 12/1973 | Monaghan | 128/2 W |
| 3,783,104 | 1/1974 | Henshilwood et al. | 435/295 |
| 3,815,580 | 6/1974 | Oster | 604/1 X |
| 3,890,954 | 6/1975 | Greenspan | 604/1 X |
| 3,913,562 | 10/1975 | Moore et al. | 435/295 |
| 3,913,564 | 10/1975 | Freshley | 604/1 |
| 3,918,435 | 11/1975 | Beall | 128/2 W |
| 3,939,044 | 2/1976 | Wilkins et al. | 435/295 |
| 3,954,563 | 5/1976 | Mennen | 435/292 |
| 4,014,322 | 3/1977 | Shah | 128/760 |
| 4,014,746 | 3/1977 | Greenspan | 604/1 |
| 4,070,249 | 1/1978 | Janin et al. | 422/102 |
| 4,073,693 | 2/1978 | Janin | 195/103.5 |
| 4,150,950 | 4/1979 | Takeguchi et al. | 422/102 X |
| 4,159,193 | 6/1979 | Gauntley et al. | 422/101 |
| 4,175,008 | 11/1979 | White | 435/295 |
| 4,175,439 | 11/1979 | Laker | 604/1 X |
| 4,184,483 | 1/1980 | Greenspan | 435/295 |
| 4,196,167 | 4/1980 | Olsen | 422/102 X |
| 4,223,093 | 9/1980 | Newman et al. | 435/295 |
| 4,268,270 | 5/1981 | Gabbay et al. | 23/230.3 |
| 4,308,028 | 12/1981 | Elkins | 422/58 X |
| 4,311,792 | 1/1982 | Avery | 435/30 |
| 4,353,868 | 10/1982 | Joalin et al. | 422/101 |
| 4,355,113 | 10/1982 | Mennen | 422/102 X |
| 4,387,725 | 6/1983 | Mull | 435/295 X |
| 4,409,988 | 10/1983 | Greenspan | 128/759 |
| 4,418,702 | 12/1983 | Brown et al. | 422/102 X |
| 4,492,305 | 1/1985 | Avery | 435/295 |
| 4,578,588 | 3/1986 | Galkin | 422/102 X |
| 4,604,360 | 8/1986 | Hounsell | 435/287 |
| 4,624,929 | 11/1986 | Ullman | 422/100 X |
| 4,635,488 | 1/1987 | Kremer | 128/760 X |
| 4,657,869 | 4/1987 | Richards et al. | 435/287 |

(List continued on next page.)

FOREIGN PATENT DOCUMENTS

| | | | |
|---|---|---|---|
| 2493515 | 5/1982 | France | 422/100 |
| 3229363A | 3/1987 | Japan | 128/760 |
| 63-293440 | 11/1988 | Japan | 128/760 |
| 2073416A | 10/1981 | United Kingdom | 128/760 |

Primary Examiner—James C. Housel
Assistant Examiner—Arlen Soderquist
Attorney, Agent, or Firm—W. Edward Johansen

[57] ABSTRACT

A fluid sampling and testing device includes a container which has a first portion and a second portion, a collecting mechanism, a removing mechanism, a sealing mechanism, an opening mechanism and a testing mechanism. The collecting mechanism collects a measured sample of a fluid and is coupled to the container in the first portion thereof. The removing mechanism removes the measured sample of the fluid from the collecting mechanism and is coupled to the container in the first portion thereof. The sealing mechanism seals the first portion of the container from the second portion. The opening mechanism opens the sealing mechanism so that the measured sample of the fluid may enter the second portion of the container from the first portion thereof. The testing mechanism tests the measured sample of the fluid and is coupled to the container in the second portion thereof.

5 Claims, 5 Drawing Sheets

U.S. PATENT DOCUMENTS

| | | | |
|---|---|---|---|
| 4,707,450 | 11/1987 | Nason | 435/295 |
| 4,717,661 | 1/1988 | McCormick et al. | 435/31 |
| 4,741,346 | 5/1988 | Wong | 128/760 |
| 4,743,537 | 5/1988 | McCormick et al. | 435/295 |
| 4,747,719 | 5/1988 | Parkin | 604/1 X |
| 4,749,655 | 6/1988 | Monthony | 435/295 |
| 4,770,853 | 9/1988 | Bernstein | 422/58 |
| 4,774,962 | 10/1988 | Hebel et al. | 128/760 |
| 4,777,964 | 10/1988 | Briggs et al. | 128/760 |
| 4,788,985 | 12/1988 | Manning et al. | 128/759 |
| 4,789,639 | 12/1988 | Fleming | 436/178 |
| 4,803,998 | 2/1989 | Kezes et al. | 128/759 |
| 4,813,432 | 3/1989 | Saint-Amand | 128/749 |
| 4,826,759 | 5/1989 | Guire et al. | 422/58 X |
| 4,859,610 | 8/1989 | Maggio | 436/518 |
| 4,865,813 | 9/1989 | Leon | 422/102 X |
| 4,871,662 | 10/1989 | Rosov | 435/30 |
| 4,895,808 | 1/1990 | Romer | 436/178 |
| 4,957,108 | 9/1990 | Schoendorfer et al. | 128/632 |
| 4,961,432 | 10/1990 | Guirguis | 128/760 |
| 4,978,504 | 12/1990 | Nason | 422/61 |
| 5,000,193 | 3/1991 | Heelis et al. | 128/760 |
| 5,063,026 | 11/1991 | Wong | 422/102 |
| 5,078,968 | 1/1992 | Nason | 422/58 |
| 5,091,316 | 2/1992 | Monthony et al. | 435/295 |
| 5,096,062 | 3/1992 | Burkardt et al. | 422/102 |
| 5,102,631 | 4/1992 | Jordan et al. | 422/42 |
| 5,103,836 | 4/1992 | Goldstein et al. | 128/760 |
| 5,188,985 | 12/1988 | Manning | 128/759 |

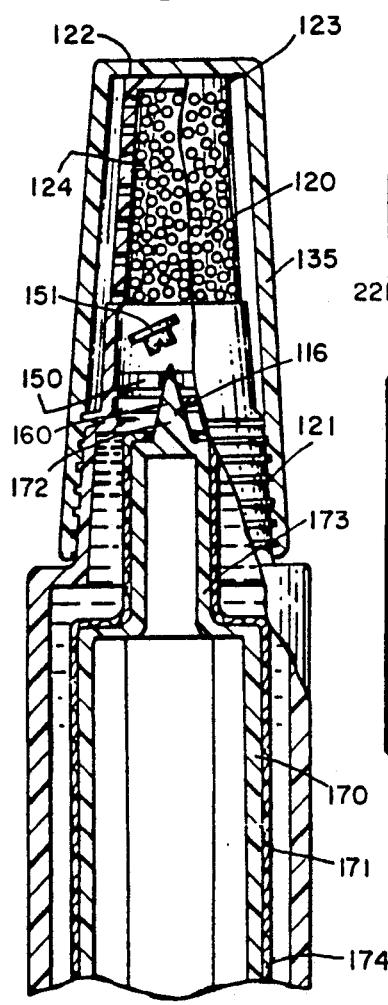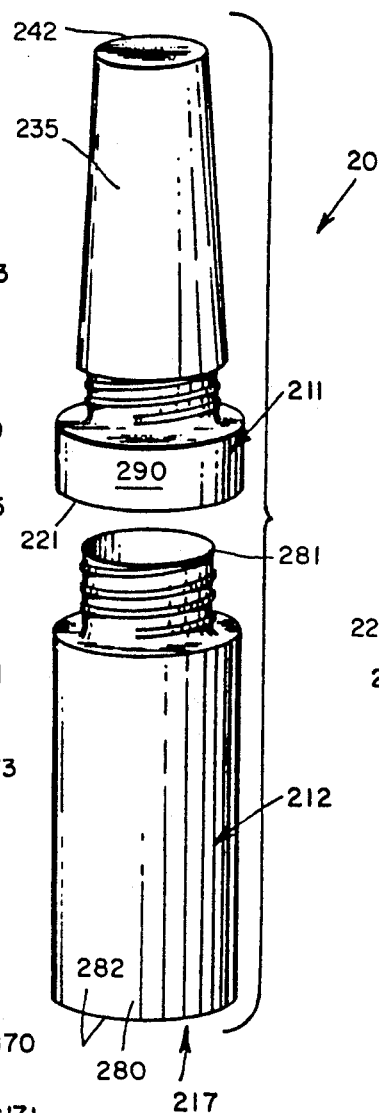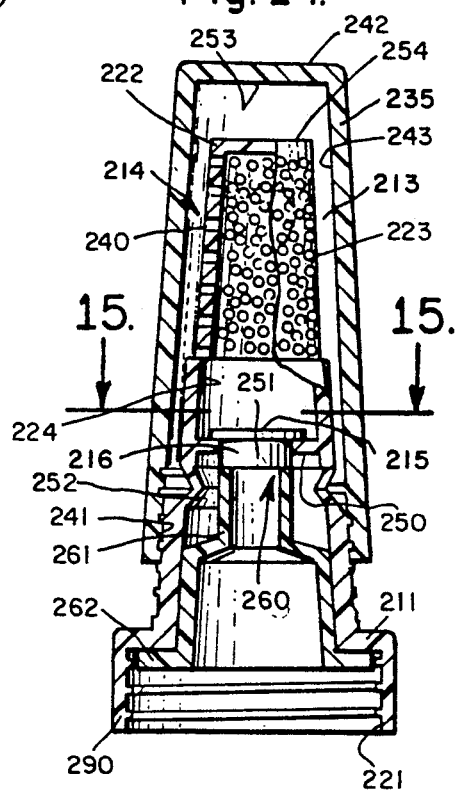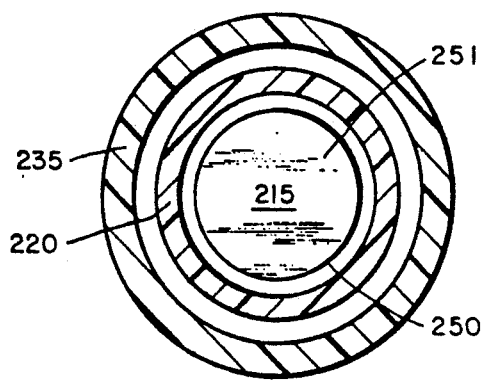

FLUID SAMPLING AND TESTING DEVICE

This application is a continuation-in-part of the application filed Dec. 18, 1990 under Ser. No. 629,278, now abandoned, which is a continuation-in-part of an application filed Jun. 25, 1991 under Ser. No. 722,333, now abandoned.

BACKGROUND OF THE INVENTION

1. Field of the Invention

The present invention relates to a saliva sampling and testing device and more particularly to a saliva sampling and testing device which not only allows a technician to collect a sample of saliva without touching the sample, but which also permits either immediate testing or transporting the collected sample of saliva to a clinical laboratory for processing and analyzing.

2. Description of the Prior Art

The current literature indicates saliva is used to conveniently, easily, safely and effectively test an individual for a variety of medical conditions. These tests for medical conditions include hepatitis screening for restaurant employees, HIV (AIDS), continue (nicotine) and cocaine screening by insurance companies and five minute HIV (AIDS) screening by dentist. Clinics for oncology, neurology, infertility, alergy orthopedic and pain which had used urine, blood and serum samples to determine the medical condition of their patients are now using sample of saliva for this same purpose.

U.S. Pat. No. 4,768,238, entitled Bifurcated Saliva Collector, issued to Israel Kleinberg and Leo M. Sreebny, on Sep. 6, 1988, teaches a bifurcated vessel for the collection of saliva. Other relevant patents include U.S. Pat. No. 4,042,337, U.S. Pat. No. 4,589,548, U.S. Pat. No. 4,580,577, U.S. Pat. No. 4,503,572, U.S. Pat. No. 3,871,230, U.S. Pat. No. 3,831,230, U.S. Pat. No. 4,589,548, U.S. Pat. No. 4,283,498 and U.S. Pat. No. 3,518,164. Navazesh and Ship have reviewed the collection of saliva in the *American Journal of Otolaryngology*, Volume 4, page 288 in 1983.

U.S. Pat. No. 4,635,488, entitled Nonintrusive Body Fluid Samplers and Methods of Using Same, issued to Richard D. Kremer on Jan. 13, 1987, teaches a body fluid sampling device which includes a hollow tube with a solid, porous, water-wettable nonfibrous nib mounted in and protrudes from one end of the tube for collecting, by absorption, a sample of a body fluid such as sweat, tears, or saliva. The sample may be extracted from the nib for analysis by supplying an extraction fluid to the interior of the tube for gravity or vacuum-assisted flow out through the nib. Alternatively, an elongated analysis element such as a strip of paper or a packed column, e.g. containing an agent that changes appearance to indicate the presence of a substance to be detected, may be disposed in the tube for endwise contact with the nib to receive the sample or components thereof by absorption.

U.S. Pat. No. 4,418,702, entitled Method and Apparatus for Collecting Saliva, issued to Paul Brown and Joseph O'Brien on Dec. 6, 1983, and U.S. Pat. No. 4,580,577, entitled Method and Apparatus for Collecting Saliva, issued to Paul Brown and Joseph O'Brien on Apr. 8, 1988, teach a method for collecting saliva from a test subject which includes providing a flavored absorbent mass, such as a sponge, for mastication and charging with saliva and then expressing the saliva from the mass. The apparatus for this method includes a barrel-piston arrangement in association with a specimen vial for storage until diagnostic testing.

U.S. Pat. No. 4,817,632, entitled Oral Fluid Collection Article, issued to Willfried Schramm on Apr. 4, 1989, teaches an oral fluid collection article for placement in the buccal cavity of an individual for the collection and filtering of a saliva fluid. The collection article has a semi-permeable membrane container enclosing an osmotic membrane.

U.S. Pat. No. 4,834,110, entitled Suction Clamped Treatment Cup Saliva Sampler, issued to Patricia A. Richard on May 30, 1989, teaches a selective collector of a human patient's saliva for monitoring or analysis is formed as a substantially conical flat concave cup of resilient molded polymer with tubing connections at an apex portal, and a large entrance portal having a soft compliant foam elastomer rim positioned for contact with the patient's soft tissue, such as the interior of the patient's cheek around the parotid salivary duct. Suction is connected to the soft foam rim, holding the concave cup in position, and suction, fixed pressure, pulsing pressure or electrical stimulation may promote the flow of saliva to a collector vessel.

U.S. Pat. No. 4,607,009, entitled Lewis Blood Group Phenotype Assay, issued on Aug. 19, 1986, teaches an assay for determining the Lewis blood group of a patient which consists of testing a body sample for the presence of Lewis antigens. Monoclonal antibodies specific for either of these antigens are employed which do not cross-react with other related antigens. Body samples which may be tested include saliva, serum, urine, and samples of paraffin-embedded tissue. Hybridoma cell lines and the antibody compositions they produce specific for these antigens are provided for use in the assay.

U.S. Pat. No. 4,720,455, entitled Progesterone Assay Method for Mammals and Monoclonal Antibody Therefor, issued to Uma M. Babu, Abdus S. Mia and Gregory D. Pancari on Jan. 19, 1988, teaches a progesterone concentration level test for mammalian body fluids particularly adapted for milk whereby estrus and pregnancy can be determined. The test can be carried out with a kit of several reagents, test tubes and a dipstick carrying an anti-progesterone monoclonal antibody.

U.S. Pat. No. 4,722,889, entitled Immunoassays Using Multiple Monoclonal Antibodies and Scavenger Antibodies, issued to Jin P. Lee, F. Salcedo and Martin F. Robins On Feb. 2, 1988, teaches a reagent kit is provided for assay of a selected antigen in an aliquot of body fluid. U.S. Pat. No. 4,452,903, entitled Assay Method and Reagent Kit Means for Lipid-containing Body Fluid, issued to Jin P. Lee and Ching Yion Jun. 5, 1984, teaches a reagent kit which is provided for assay of a selected hapten in an aliquot of body fluid containing lipid.

U.S. Pat. No. 4,769,216, entitled Device for Detecting Antigens and Antibodies, issued to Howard M. Chandler, Kevin Healey and John G. Hurrell on Sep. 6, 1988, teaches a device for use in detecting or determining the presence of antigenic or haptenic substances or antibodies in a sample which includes a plurality of tubular or capillary elements, each having antibodies or antigenic or haptenic substances attached to an internal surface thereof, and mechanism for causing fluids to pass simultaneously or sequentially through the plurality of capillary elements. A method and test kit for detecting and determining the presence of antigenic or haptenic substances or antibodies in a sample by the enzyme-linked immunosorbent assay technique is characterized by use of urease as the enzyme in an antibody-enzyme or antigen-enzyme conjugate, with urea being used as the enzyme substrate.

U.S. Pat. No. 4,857,456, entitled Assay of Bone Morphogenetic Protein (BMP) and Anti-BMP Antibody for the Diagnosis of Bone Disorders, issued to Marshall R. Urist on Aug. 15, 1989, teaches a diagnostic kit and a method for diagnosing bone disorders which includes assaying bone morphogenetic protein or anti-bone morphogenetic protein antibody in body fluids. The diagnosis may be carried out by comparing either the bone morphogenetic protein and the anti-bone morphogenetic protein antibody or the ratio of the two to normal assay standards.

U.S. Pat. No. 4,771,486, entitled Sputum Specimen Collecting Device, issued to Charles N. Gutierrez and David Vigil on Sep. 20, 1988, teaches a sputum sampling device having capability for sputum-saliva separation which includes a substantially circular cup having a wall portion which tapers inwardly from top to bottom, a separation plate having a substantially elliptical planar configuration, the major and minor axis of the plate being dimensioned to allow insertion of the plate down into the cup at a slant to position the lower portion of the plate a distance above the bottom of the cup, a plurality of apertures formed in the lower portion of the plate to provide saliva drainage ports, and an upper portion of the plate comprising a roughened textured surface for retracting and holding sputum in position for recovery in order to obtain a sensory and microbiological examination.

U.S. Pat. No. 4,853,325, entitled Saliva Test for Feline Leukemia Virus, issued to Morton A. Vodian, Eric S. Bean and Eric D. LeMoine on Aug. 1, 1989, teaches a saliva test for feline leukemia virus (FeLV) which employs a probe having an immunochemically sensitive member for collecting saliva from the oral cavity of a cat and which employs ELISA reagents for the incubation of the probe and the development of color reactions to indicate the presence or absence of FeLV within the saliva sample collected onto the probe.

U.S. Pat. No. 4,468,470, entitled Method and a Kit for the Assay of Antibodies to Soluble Antigens, issued to Robertus C. Aalberse on Aug. 28, 1984, teaches a method for the assay of antibodies to soluble antigens in an aqueous sample, in particular in body fluids, such as blood serum or blood plasma. The sample is contacted with an antigen in vitro so that antibodies, if present, are bound by the antigens.

U.S. Pat. No. 4,929,544, entitled Reagents, Methods, and Test Kit for Diagnosing/monitoring Cancer in Humans, issued to Barbara S. Vold on May 29, 1990, teaches that a quantitative immunoassay is used to diagnose/monitor human cancer by measuring a physiological fluid specimen of a subject. The quantitative immunoassay employs a monoclonal antibody and either compares that level to the level which occurs in corresponding physiological fluid of normal subjects to determine whether the former is substantially elevated over the latter or compares that level to the level of present in specimens taken from the subject at different times.

U.S. Pat. No. 4,942,122, entitled AIDS Prognosis Test Detecting the Presence of Antibodies Inhibiting HIV Reverse Transcriptase, issued to David T. Imagawa, Moon H. Lee and Kouichi Sano on Jul. 17, 1990, teaches a kit detects the presence of an antibody inhibiting HIV reverse transcriptase. The amount of antibody inhibiting HIV reverse transcriptase present in the body fluids of a patient known to be immunopositive for HIV gives the clinician a means to form a prognosis for each individual case.

U.S. Pat. No. 4,447,528, entitled Detecting Intrinsic Factor Blocking Site Antibody, issued to James E. Ellis, Graham P. Lidgard, Gerald Odstrchel and Louis J. Riceberg on May 8, 1984, teaches a radioassay reagent kit therefor which is for detecting auto blocking antibody, such as auto blocking antibody which interferes with the complexation of intrinsic factor with a vitamin. A receptor, i.e., intrinsic factor, is immobilized on a support and the amount of ligand, i.e., vitamin, capable of binding therewith in the presence of a biological fluid sample is determined.

U.S. Pat. No. 4,865,966, entitled Method for Detecting Antibodies to Human Immunodeficiency Virus, issued to Alvin E. Friedman-Kien and Yunzhen Cao on Sep. 12, 1989, teaches in a method of screening mammals for antibodies to viral agents a urine sample is collected from a mammal to be tested. The urine sample is assayed the sample for antibodies directed against the specific viral agent.

SUMMARY OF INVENTION

In view of the foregoing factors and conditions which are characteristic of the prior art it is the primary object of the present invention to provide a saliva sampling and testing device which allows a technician to collect a sample of saliva without touching the sample.

It is another object of the present invention to provide a saliva sampling and testing device for collecting a sample of a saliva which permits immediate testing.

It is still another object of the present invention to provide a saliva sampling and testing device for collecting a sample of a saliva which permits transportation of the collected sample of saliva to a clinical laboratory for processing and analyzing.

It is still another object of the present invention to provide a saliva sampling and testing device for collecting a sample of a saliva which enables clinics for oncology, neurology, infertility, allergy, orthopedic surgery and pain, which had used urine, blood and serum samples to determine the medical condition of their patients, to use samples of saliva.

It is yet another object of the present invention to provide a fluid sampling and testing device which allows a technician to collect a sample of fluid without touching the sample.

In accordance with the present invention an embodiment of a fluid sampling and testing device is described. The fluid sampling and testing device includes a container which has a first portion and a second portion, a collecting mechanism, a removing mechanism, a sealing mechanism, an opening mechanism and a testing mechanism. The collecting mechanism collects a measured sample of a fluid and is coupled to the container in the first portion thereof. The removing mechanism removes the measured sample of the fluid from the collecting mechanism and is coupled to the container in the first portion. The sealing mechanism seals the first portion of the container from the second portion. The opening mechanism opens the sealing mechanism so that the measured sample of the fluid may enter the second portion of the container from the first portion thereof. The testing mechanism tests the measured sample of the fluid and is coupled to the container in the second portion thereof.

Other claims and many of the attendant advantages will be more readily appreciated as the same becomes better understood by reference to the following detailed description and considered in connection with the accompanying drawing in which like reference symbols designate like parts throughout the figures.

The features of the present invention which are believed to be novel are set forth with particularity in the appended claims.

DESCRIPTION OF THE DRAWING

FIG. 12 is a longitudinal view in cross-section of the second fluid sampling and testing device.

FIG. 13 is a perspective view of a first fluid sampling and transporting device which is used for collecting a measured sample of a fluid and which has been constructed in accordance with the principles of the third embodiment of the present invention.

FIG. 14 is a partial longitudinal view in cross-section of the first fluid sampling and transporting device of FIG. 13.

FIG. 15 is a transverse view in cross-section of the second fluid sampling and testing device of FIG. 13 taken along line 15—15 of FIG. 14.

DESCRIPTION OF THE PREFERRED EMBODIMENT

Figure 1:
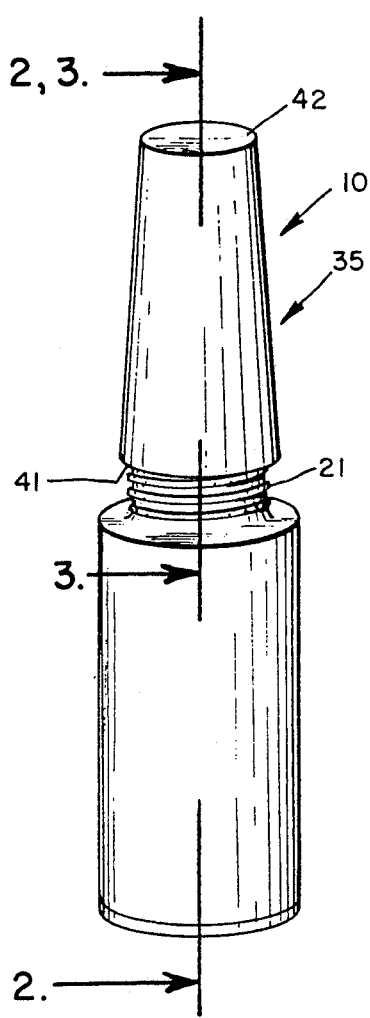
FIG. 1 is a perspective view of a first fluid sampling and testing device which is used for collecting a measured sample of a fluid and which has been constructed in accordance with the principles of the first embodiment of the present invention.
Figure 2:
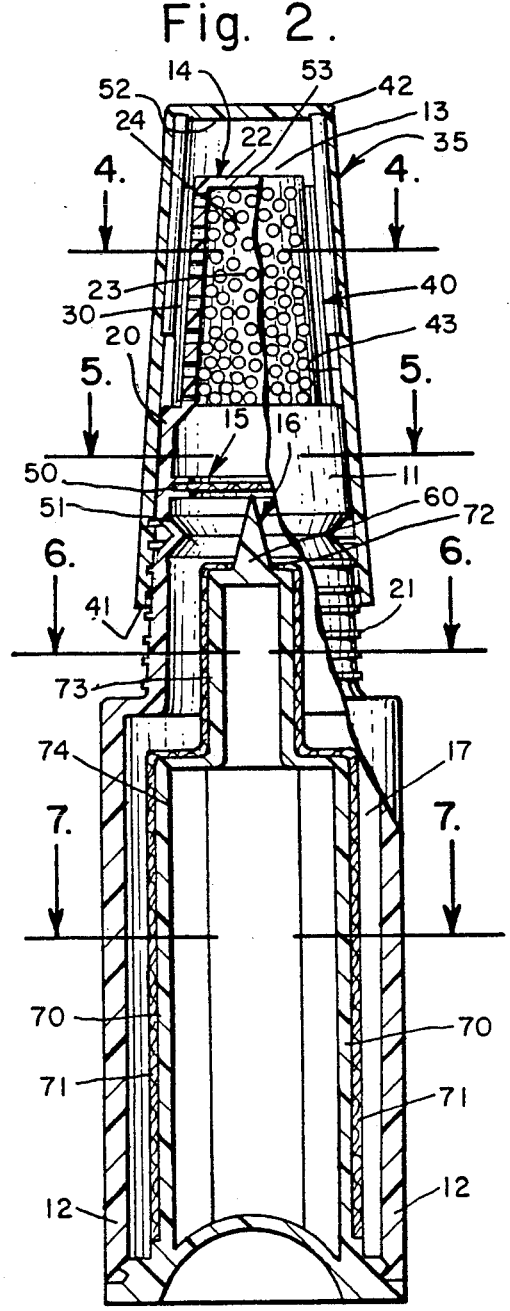
FIG. 2 is a longitudinal view in cross-section of the first fluid sampling and testing device of FIG. 1.
Figure 3:
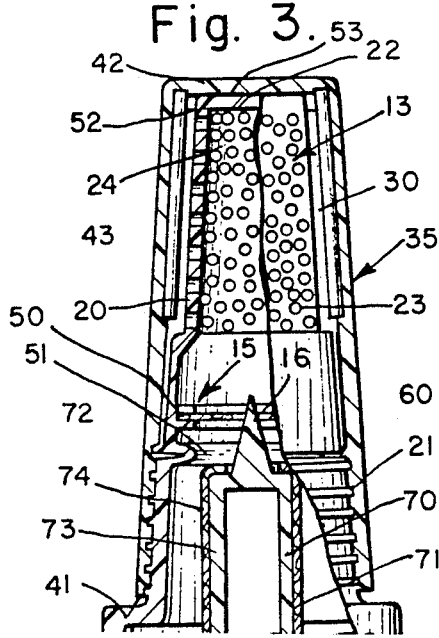
FIG. 3 is a partial longitudinal view in cross-section of the first fluid sampling and testing device of FIG. 1.
Figure 4:
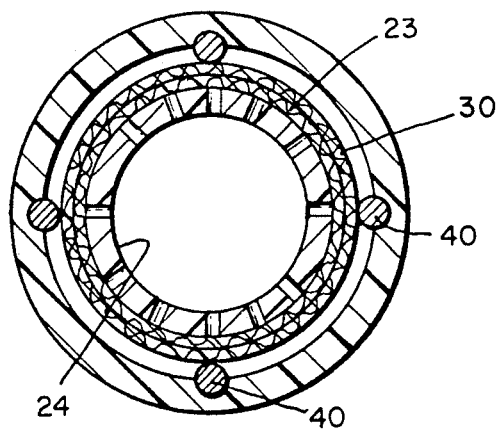
FIG. 4 is a transverse view in cross-section of the first fluid sampling and testing device of FIG. 1 taken along line 4—4 of FIG. 2.
Figure 5:
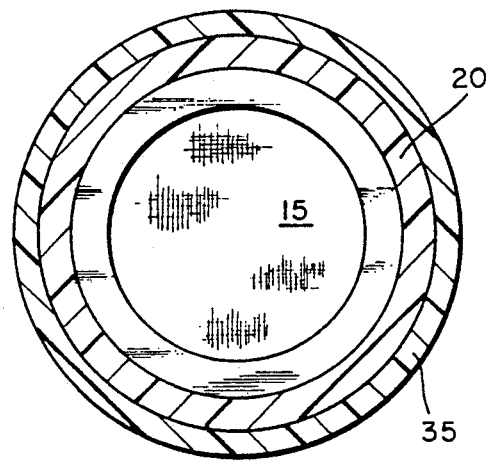
FIG. 5 is a transverse view in cross-section of the first fluid sampling and testing device of FIG. 1 taken along line 5—5 of FIG. 2.
Figure 6:
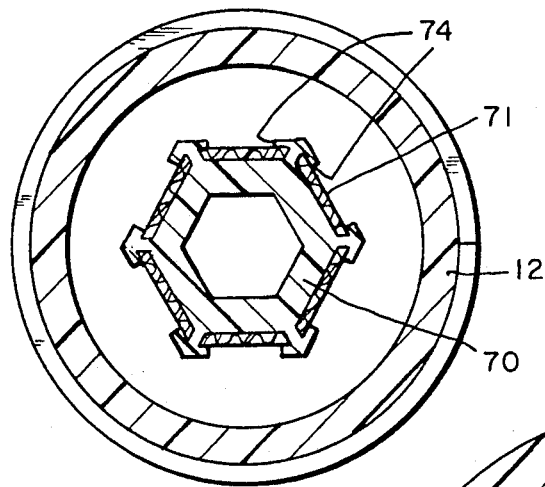
FIG. 6 is a transverse view in cross-section of the first fluid sampling and testing device of FIG. 1 taken along line 6—6 of FIG. 2.
Figure 7:
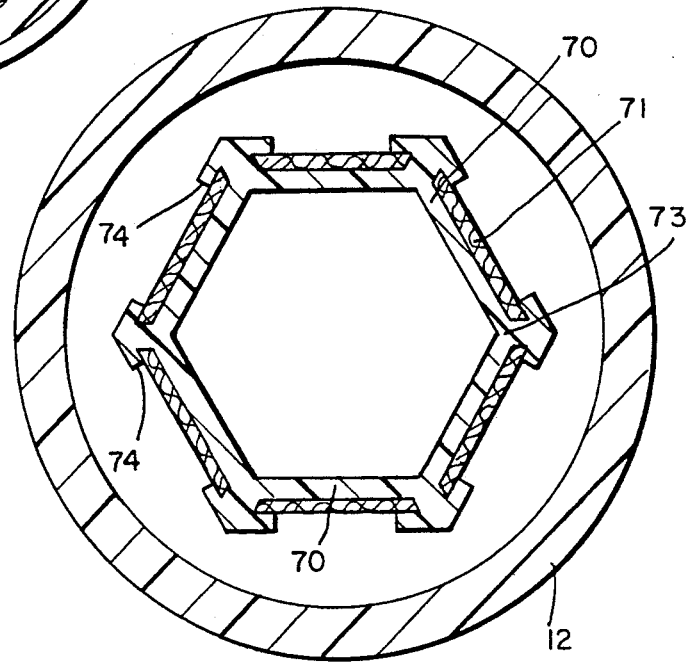
FIG. 7 is a transverse view in cross-section of the first fluid sampling and testing device of FIG. 1 taken along line 7—7 of FIG. 2.

In order to best understand the present invention it is necessary to refer to the following description of the preferred embodiment in conjunction with the accompanying drawing. Referring to FIG. 1 in conjunction with FIG. 2 a first fluid sampling and testing device 10 includes a container which has a first portion 11 and a second portion 12, a first collecting mechanism 13, a first removing mechanism 14, a first sealing mechanism 15, a first opening mechanism 16 and a first testing mechanism 17. The first collecting mechanism 13 collects a measured sample of a fluid and is coupled to the container in the first portion 11 thereof. The first removing mechanism 14 removes the measured sample of the fluid from the first collecting mechanism 13 and is coupled to the container in the first portion 11 thereof. The first sealing mechanism 15 seals the first portion 11 of the container from the second portion 12. The first opening mechanism 16 opens the first sealing mechanism 15 so that the measured sample of the fluid may enter the second portion 12 of the container from the first portion 11 thereof. The first testing mechanism 17 tests the measured sample of the fluid and is coupled to the container in the second portion 12 thereof.

Still referring to FIG. 1 in conjunction with FIG. 2, FIG. 3, FIG. 4, FIG. 5, FIG. 6 and FIG. 7 the first portion 11 of the container is a hollow, truncated cone 20 which has an open threaded end 21, a closed end 22, a holey outer surface 23 and an inner surface 24. The first collecting mechanism 13 includes a piece 30 of filter paper which is of predetermined dimensions. The piece 30 of filter paper is mechanically coupled to the hollow, truncated cone 20 and is disposed on the holey outer surface thereof 23. The first removing mechanism 14 includes a cap 35 and a pressing mechanism 40. The cap 35 has a threaded open end 41, a closed end 42 and an inner surface 43. The threaded open end 41 of the cap 35 is adapted to be threadedly coupled to the threaded, open end 21 of the hollow, truncated cone 20 so that the piece 30 of filter paper is disposed between the inner surface 43 of the cap 35 and the holey outer surface 23 of the hollow, truncated cone 20. The pressing mechanism 40 presses the piece 30 of filter paper and is disposed between the inner surface 43 of the cap 35 and the holey outer surface 23 of the hollow, truncated cone 20 and is mechanically coupled to the piece 30 of filter paper. The first sealing mechanism 15 is a membrane 50 which is disposed adjacent to the open, threaded end 21 of the hollow, truncated cone 20 on the inner surface 24 thereof. The hollow, truncated cone 20 has a collapsible portion 51 so that the inner top 52 of the ca 35 engages the outer top 53 of the hollow, truncated cone 20 as the cap 35 is being threaded downward causing the collapsible portion 51 thereof to collapse to allow the ca 35 to continue to be threaded downward. The first opening mechanism 16 includes a breaking mechanism 60 which breaks the membrane 50 when the cap 35 is threaded downward. The testing mechanism 17 includes a first testing pole 70 and a plurality of reagent test strips 71. The first testing pole 70 is disposed in the second portion 12 of the container and has a first portion 72 which functions as the breaking mechanism 60 and a second portion 73 which forms channels 74 through which the measured amount of the fluid flows. Each reagent test strip 71 is mechanically coupled to the first testing pole 70 and contacts a portion of the measured amount of the fluid as it flows in the channels 74.

Figure 8:
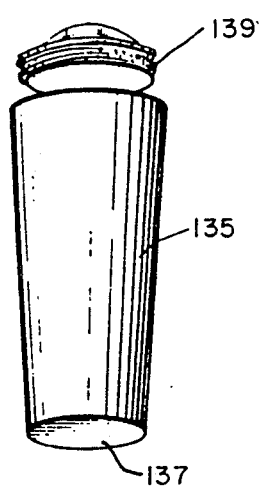
FIG. 8 is a perspective view of a cap and a lid of a second fluid sampling and testing device which is used for collecting a measured sample of a fluid and which has been constructed in accordance with the principles of the second embodiment of the present invention.
Figure 9:
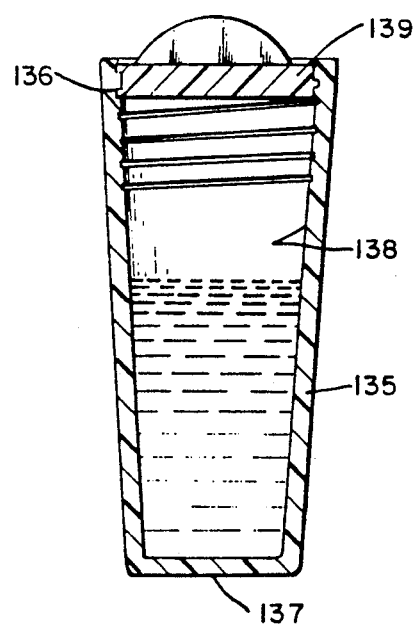
FIG. 9 is a longitudinal view in cross-section of the cap and the lid of FIG. 8 of the second fluid sampling and testing device.
Figure 10:
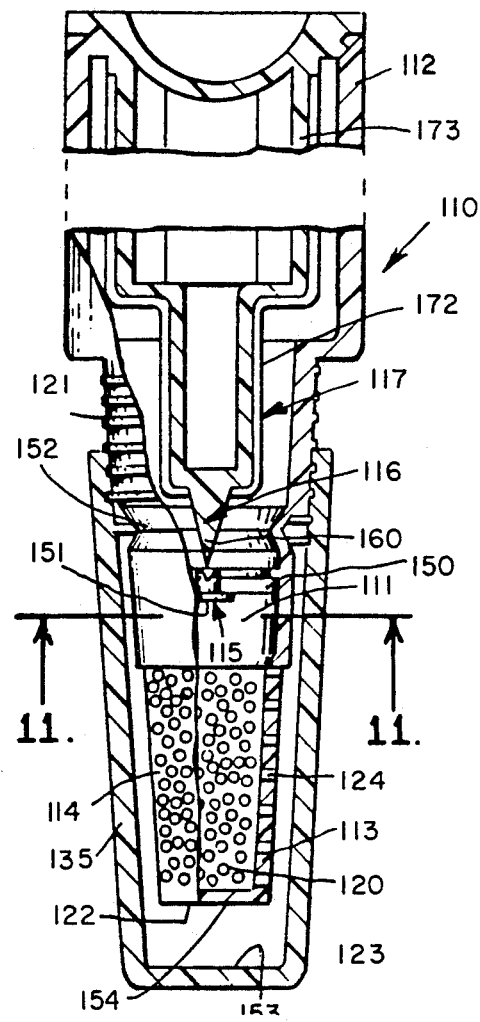
FIG. 10 is a longitudinal view in cross-section of the second fluid sampling and testing device.

Referring to FIG. 8 in conjunction with FIG. 9 and FIG. 10 a second fluid sampling and testing device 110 includes a container which has a first portion 111 and a second portion 112, a second collecting mechanism 113, a second removing mechanism 114, a second sealing mechanism 115, a second opening mechanism 116 and a second testing mechanism 117. The second collecting mechanism 113 collects a measured sample of a fluid and is coupled to the container in the first portion 111 thereof. The second removing mechanism 114 removes the measured sample of the fluid from the second collecting mechanism 113 and is coupled to the container in the first portion 111 thereof. The second sealing mechanism 115 seals the first portion 111 of the container from the second portion 112. The second opening mechanism 116 opens the second sealing mechanism 115 so that the measured sample of the fluid may enter the second portion 112 of the container from the first portion 111 thereof. The second testing mechanism 117 tests the measured sample of the fluid and is coupled to the container in the second portion 112 thereof.

Figure 11:
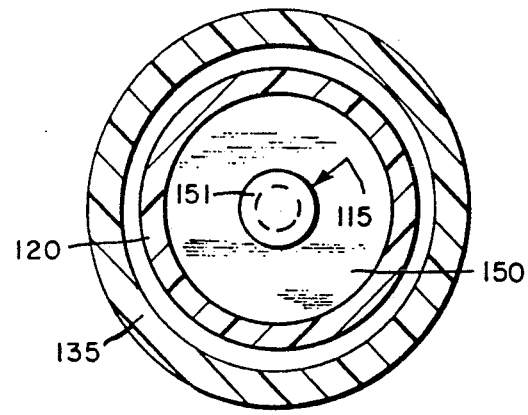
FIG. 11 is a transverse view in cross-section of the second fluid sampling and testing device of FIG. 8 taken along line 11—11 of FIG. 10.

Still referring to FIG. 10 in conjunction with FIG. 11 and FIG. 12, the first portion 111 of the container is a hollow, truncated cone 120 which has an open threaded end 121, a closed end 122, a holey outer surface 123 and an inner surface 124. The second collecting mechanism 113 includes a cap 135 which has a threaded open end 136, a closed end 137 and an inner surface 138. The threaded open end 121 of the cap 120 is adapted to be threadedly coupled to both a threaded lid 139 and the open end 121 of the hollow, truncated cone 120 so that the measured amount of fluid is disposed between the inner surface 138 of the cap 135 and the holey outer surface 123 of the hollow, truncated cone 120. The second sealing mechanism 115 is a first flange 150 and a first plug 151. The first flange 150 is disposed adjacent to the open, threaded end 121 of the hollow, truncated cone 120 on the inner surface 124 thereof. The first plug 151 is disposed in the first flange 150 and snugly, but removably coupled thereto. The hollow, truncated cone 120 has a collapsible portion 152 so that the inner top 153 of the cap 135 engages the outer top 154 of the hollow, truncated cone 120 as the cap 135 is being threaded downward causing the collapsible portion 152 thereof to collapse to allow the cap 135 to continue to be threaded downward. The second opening mechanism 116 includes a first lifting mechanism 160 which lifts the first plug 151 from the first flange 150 when the cap 135 is threaded downward. The second testing mechanism 117 includes a second testing pole 170 and a plurality of reagent test strips 171 The second testing pole 170 is disposed in the second portion 112 of the container and has a first portion 172 which functions as the first lifting mechanism 160 and a second portion 173 which forms channels 174 through which the measured amount of the fluid flows. Each reagent test strip 171 is mechanically coupled to the second testing pole 170 and contacts a portion of the measured amount of the fluid as it flows in the channels 174.

Referring to FIG. 13 in conjunction with FIG. 14 and FIG. 15 a first fluid sampling and transporting device 210 includes a container which has a first portion 211 and a second portion 212, a third collecting mechanism 213, a third removing mechanism 214, a first sealing mechanism 215, a third opening mechanism 216 and a first transporting mechanism 217. The third collecting mechanism 213 collects a measured sample of a fluid and is coupled to the container in the first portion 211 thereof. The third removing mechanism 214 removes the measured sample of the fluid from the third collecting mechanism 213 and is coupled to the container in the first portion 211 thereof. The third sealing mechanism 215 seals the first portion 211 of the container from the second portion 212. The third opening mechanism 216 opens the third sealing mechanism 215 so that the measured sample of the fluid may enter the second portion 212 of the container from the first portion 211 thereof. The first transporting mechanism 217 is mechanically coupled to the container in the second portion 212 thereof.

Still referring to FIG. 13 in conjunction with FIG. 14 and FIG. 15 the first portion 211 of the container is a hollow, truncated cone 220 which has an open threaded end 221, a closed end 222, a holey outer surface 223 and an inner surface 224. The third collecting mechanism 213 includes a piece 230 of filter paper which is of predetermined dimensions. The piece 230 of filter paper is mechanically coupled to the hollow, truncated cone 220 and is disposed on the holey outer surface thereof 223. The third removing mechanism 214 includes a cap 235 and a pressing mechanism 240. The cap 235 has a threaded open end 241, a closed end 242 and an inner surface 243. The threaded open end 241 of the cap 235 is adapted to be threadedly coupled to the threaded, open end 221 of the hollow, truncated cone 220 so that the piece 230 of filter paper is disposed between the inner surface 243 of the cap 235 and the holey outer surface 223 of the hollow, truncated cone 220. The pressing mechanism 240 presses the piece 230 of filter paper and is disposed between the inner surface 243 of the cap 235 and the holey outer surface 223 of the hollow, truncated cone 220 and is mechanically coupled to the piece 230 of filter paper. The third sealing mechanism 215 is a second flange 250 and a second plug 251. The second flange 250 is disposed adjacent to the open, threaded end 221 of the hollow, truncated cone 220 on the inner surface 224 thereof. The second plug 251 is disposed in the second flange 250 and snugly, but removably coupled thereto. The hollow, truncated cone 220 has a collapsible portion 252 so that the inner top 253 of the cap 235 engages the outer top 254 of the hollow, truncated cone 220 as the cap 235 is being threaded downward causing the collapsible portion 252 thereof to collapse to allow the cap 235 to continue to be threaded downward. The third opening mechanism 216 includes a second lifting mechanism 260 which is a lifting collar 261 with a flange 262 and which lifts the second plug 251 from the second flange 250 when the cap 235 is threaded downward. The first transporting mechanism 217 is a sample bottom 280 with a threaded, open end 281 and a closed end 282. The second portion 212 is a collar 290 with a threaded inner surface. The sample bottom 280 is threadedly coupled to the collar 290 with the lifting collar inserted into the collar 280.

Figure 16:
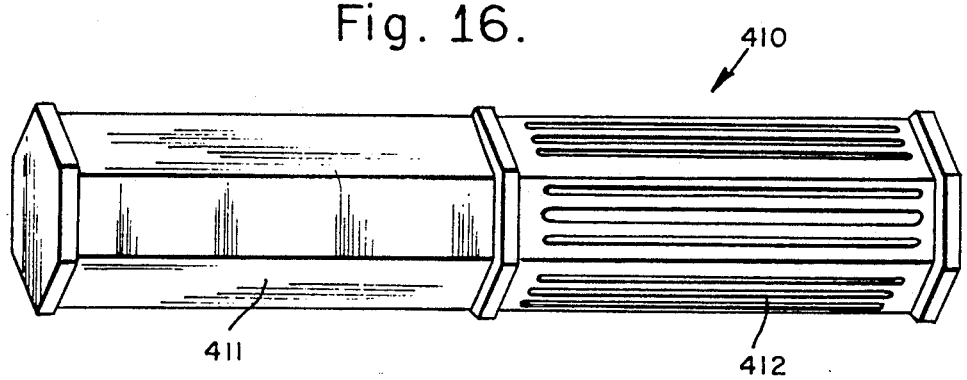
FIG. 16 is a perspective view of a third fluid sampling and testing device which is used for collecting a measured sample of a fluid and which has been constructed in accordance with the principles of the fourth embodiment of the present invention.
Figure 17:
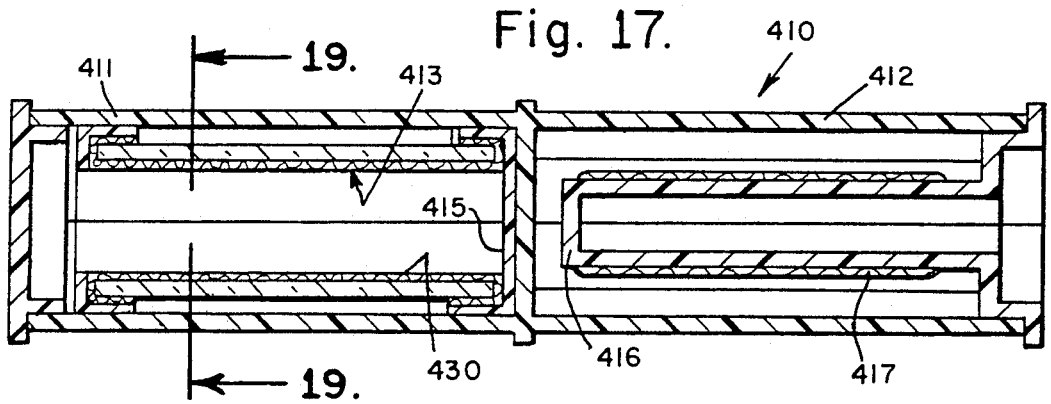
FIG. 17 is a first longitudinal view in cross-section of the third fluid sampling and testing device of FIG. 16.
Figure 18:
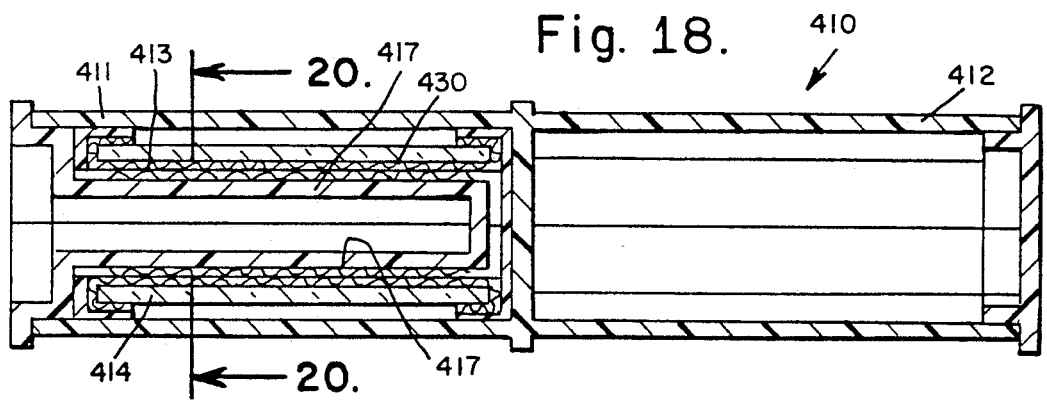
FIG. 18 is a second longitudinal view in cross-section of the third fluid sampling and testing device of FIG. 16.

Referring to FIG. 16 in conjunction with FIG. 17 and FIG. 18 a third fluid sampling and testing device 410 includes a container which has a first portion 411 and a second portion 412, a fourth collecting mechanism 413, a fourth removing mechanism 414, a fourth sealing mechanism 415, a fourth opening mechanism 416 and a fourth testing mechanism 417. The fourth collecting mechanism 413 collects a measured sample of a fluid and is coupled to the container in the first portion 411 thereof. The fourth removing mechanism 414 removes the measured sample of the fluid from the fourth collecting mechanism 413 and is coupled to the container in the first portion 411 thereof. The fourth sealing mechanism 415 seals the first portion 411 of the container from the second portion 412. The fourth opening mechanism 416 opens the fourth sealing mechanism 415 so that the measured sample of the fluid may enter the second portion 412 of the container from the first portion 411 thereof. The third testing mechanism 417 tests the measured sample of the fluid and is coupled to the container in the second portion 412 thereof.

Figure 19:
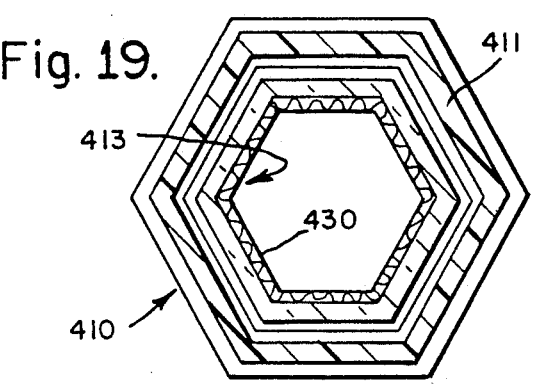
FIG. 19 is a transverse view in cross-section of the third fluid sampling and testing device of FIG. 16 taken along line 19—19 of FIG. 17.
Figure 20:
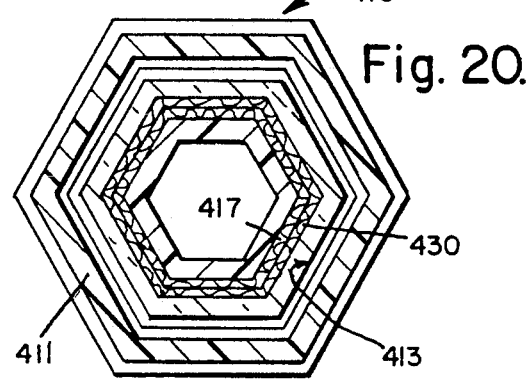
FIG. 20 is a transverse view in cross-section of the third fluid sampling and testing device of FIG. 16 taken along line 20—20 of FIG. 18.

Still referring to FIG. 17 in conjunction with FIG. 18, FIG. 19 and FIG. 20 the first portion 411 of the container has a fourth collecting mechanism 413 which includes a piece 430 of filter paper which is of predetermined dimensions. The piece 430 of filter paper is mechanically is disposed on the fourth removing mechanism 414.

From the foregoing it can be seen that a fluid sampling and testing device is used for collecting a measured sample of a fluid has been described. It should be noted that the sketches are not drawn to scale and that distance of and between the figures are not to be considered significant.

Accordingly it is intended that the foregoing disclosure and showing made in the drawing shall be considered only as an illustration of the principle of the present invention.

What is claimed is:

1. A fluid sampling and testing device comprising:
  a. a container having a first portion and a second portion wherein said first portion of said container is a hollow, truncated cone having an open threaded end, a closed end, a wall with an outer surface and an inner surface with holes therethrough connecting the open threaded end and the closed end;
  b. collecting means for collecting a measured amount of sample fluid, said collecting means comprising a piece of filter paper which is mechanically coupled to said hollow, truncated cone being disposed on said outer surface of the wall covering said holes;
  c. removing means for removing said measured amount of sample fluid from said piece of filter paper, said removing means being coupled to said container;
  d. a seal which seals said first portion of said container from said second portion thereof;
  e. an opener which opens said seal so that said measured amount of sample fluid may enter said second portion of said container from said first portion thereof; and
  f. a tester which tests said measured amount of sample fluid, said tester being coupled to said container in said second portion thereof.

2. A fluid sampling and testing device according to claim 1 wherein said removing means comprises:
  a. a cap which has a threaded open end, a closed end and an inner surface and said threaded open end of which can be threadedly coupled to said threaded open end of said hollow, truncated cone whereby said piece of filter paper is disposed between said inner surface of said cap and said outer surface of said hollow, truncated cone; and
  b. pressing means for pressing said piece of filter paper, said pressing means being disposed between said inner surface of said cap and said outer surface of said hollow, truncated cone and mechanically coupled to said piece of filter paper.

3. A fluid sampling and testing device according to claim 2 wherein said seal is a membrane which is disposed adjacent to said open, threaded end of said hollow, truncated cone on said inner surface thereof.

4. A fluid sampling and testing device according to claim 3 wherein said hollow, truncated cone has a collapsible portion so that the inner top of said cap engages the outer top of said hollow, truncated cone as said cap is being threaded downward causing said collapsible portion thereof to collapse to allow said cap to continue to be threaded downward and said opening means comprises breaking means for breaking said membrane when said cap is threaded downward.

5. A fluid sampling and testing device according to claim 4 wherein said testing means comprises:
  a. a testing pole which is disposed in said second portion of said container and which has a first portion which functions as said breaking means and a second portion which forms channels through which the measured amount of sample fluid flows; and
  b. a plurality of reagent test strips each of which is mechanically coupled to said testing pole and each of which contacts the measured amount of sample fluid as it flows in said channels.

* * * * *